(12) United States Patent
Bravo et al.

(10) Patent No.: US 11,540,921 B2
(45) Date of Patent: Jan. 3, 2023

(54) SYSTEM AND METHOD FOR FABRICATING CARTILAGE IMPLANTS

(71) Applicants: CARNEGIE MELLON UNIVERSITY, Pittsburgh, PA (US); University of Pittsburgh—Of the Commonwealth System of Higher Education, Pittsburgh, PA (US)

(72) Inventors: Liliana Camison Bravo, Pittsburgh, PA (US); Phil G. Campbell, Pittsburgh, PA (US); Toygun Cetinkaya, Pittsburgh, PA (US); O. Burak Ozdoganlar, Sewickley, PA (US); Lucas A. Dvoracek, Pittsburgh, PA (US); Jesse A. Goldstein, Pittsburgh, PA (US)

(73) Assignees: Carnegie Mellon University, Pittsburgh, PA (US); University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 90 days.

(21) Appl. No.: 17/220,575

(22) Filed: Apr. 1, 2021

(65) Prior Publication Data
US 2021/0307912 A1 Oct. 7, 2021

Related U.S. Application Data

(60) Provisional application No. 63/003,582, filed on Apr. 1, 2020.

(51) Int. Cl.
*A61F 2/30* (2006.01)

(52) U.S. Cl.
CPC ...... *A61F 2/30942* (2013.01); *A61F 2/30756* (2013.01); *A61F 2002/3096* (2013.01); *A61F 2002/30948* (2013.01)

(58) Field of Classification Search
CPC .............. A61F 2/30942; A61F 2/30756; A61F 2002/3096; A61F 2002/30948
See application file for complete search history.

(56) References Cited

U.S. PATENT DOCUMENTS

D781,421 S 3/2017 Reinisch
2020/0368867 A1* 11/2020 Li ...................... B23Q 11/1076

FOREIGN PATENT DOCUMENTS

WO 2018200816 A1 11/2018

* cited by examiner

*Primary Examiner* — Jason-Dennis N Stewart
(74) *Attorney, Agent, or Firm* — Michael G. Monyok

(57) ABSTRACT

A system and method used to fabricate an implant from cartilage, where the implant can be used in reconstructive surgery. The system includes a thermoregulation device capable of maintaining a desired temperature range during milling operations. The milling machine is controlled by instructions generated from a digital model of the implant. The digital model can be a stock model or a custom model created from medical scans.

13 Claims, 6 Drawing Sheets

SYSTEM AND METHOD FOR FABRICATING CARTILAGE IMPLANTS

CROSS-REFERENCE TO RELATED APPLICATIONS

This application claims the benefit under 35 U.S.C. § 119 of Provisional Application Ser. No. 63/003,582, filed Apr. 1, 2020, which is incorporated herein by reference.

STATEMENT REGARDING FEDERALLY SPONSORED RESEARCH

Not applicable.

BACKGROUND OF THE INVENTION

The present disclosure is related generally to implants used in reconstructive surgery. More specifically, the disclosure relates to a system and method used to fabricate implants from human cartilage through a micromilling process, where the implants can be used in surgeries such as ear reconstruction.

The face is the critical identifying feature of humans, and facial deformities can have profound effects on self-confidence, social interaction, and psychological development. Facial deformities could also cause functional problems, such as inability to wear prescription glasses or respiratory masks. When critical facial features such as the ears or nose are absent or deformed due to congenital conditions or acquired injury (e.g., trauma, bites, burns, or malignancy), surgical reconstruction becomes essential to restore the patient's wholeness, and with it, improved quality of life. However, accurately reconstructing three dimensional (3D) features like the ears or nose (among others body parts) can be exceedingly difficult, with current options being suboptimal.

Reconstruction of the human ear is an example of a particularly difficult reconstructive surgery given the complex 3D geometry of the ear. Currently, surgeons perform ear reconstruction through one of two methods, both of which present significant risks to the patient. In one method, the surgeon uses autologous cartilage obtained from a donor site on the patient, typically the ribs, and manually sculpts the cartilage into a shape resembling the cartilage of an ear. This method is time consuming, and both artistically and technically demanding for the surgeon. It also carries a great burden for the patient in terms of donor site morbidity, with the likelihood of an unrealistic reconstruction depending on the surgeon's skill to sculpt, and the prospect of multiple surgeries until completion. In a second method, prefabricated synthetic implants, typically porous polyethylene, are used. The prefabricated implants can match the natural shape of the patient's ear and do not require an artistically skilled surgeon but carry the risk of dangerous complications that are difficult to predict or control. Within the first decade after implantation of the synthetic ear, complication rates above 6% (extrusion, infection, fracture, etc.) are typical. Due to the lack of long-term viability, synthetic implants are especially impractical for pediatric patients. Accordingly, the difficulties for ear reconstruction have resulted in few surgeons offering ear reconstruction at all worldwide. These challenges are not unique to ears and apply to other body parts.

Robotics and computer-aided tools have been utilized by surgeons to improve the outcomes of many surgical procedures, including surgeries requiring precision shaping of body tissue. For example, surgeons performing total knee arthroplasty may utilize 'intelligent instruments' for the bone milling process. However, when used on bodily tissue in the operating room, the milling process is limited to bone and other hard materials. These techniques are not straightforward to adapt to other tissues, and thus, they have not been used for cartilage and other soft tissues encountered in facial reconstruction surgeries.

In another example of a current application, CNC milling is used in facial reconstruction for the creation of patient-specific synthetic prosthesis (e.g., porous polyethylene cranial implants in cranioplasty) or for creation of custom surgical parts (e.g. plates and screws for a facial fracture), but these techniques have not been used for the creation of custom-made implants from human or animal tissues.

Bioengineered materials have also been proposed for use in facial reconstruction surgeries. Unlike autologous or cadaveric cartilage, bioengineered materials lack structural stability. Under the pressure of the overlying skin, bioengineered or matrix-grown cartilage resorbs within weeks or months. Therefore, it would be advantageous to develop a system and method for facial reconstruction that provides the benefits of autologous tissue integration with the practicality of prefabricated implants.

BRIEF SUMMARY

According to embodiments of the present disclosure is a system and method used to fabricate an implant using human cadaveric cartilage. This method can be applied to tissue obtained from other sources, such as cartilage obtained from a donor animal. Frozen "blank" pieces of preprocessed cadaveric or animal cartilage are shaped with a high-precision three-dimensional (3D) computer numerical controlled (CNC) micromilling machine prior to implantation. Keeping the cartilages within a prescribed temperature range is necessary to ensure their viability. This temperature is commonly within the range of −40 to −20 deg. C. For this purpose, temperature and other environmental control systems are implemented during the micromilling operation to prevent damage to the cartilage. As such, the method comprises a freeze micromilling process. The cartilage implant can be shaped in a frozen state and then preserved in a frozen state until the time of surgery, where it is implanted into the patient as in the standard approach for the respective operation (e.g., under the mastoid skin or a temporoparietal flap plus skin graft for ear reconstruction). This process can be applied to areas where cartilage is missing or defective, such as the ear, nose, airways, replacements for carpal hand bones, or other parts requiring structural support, form change, or augmentation.

The freeze micromilling system and method bring clear advantages, including: 1) elimination of donor site morbidity, while still offering a non-synthetic alternative; 2) reduction in the number of surgeries, bringing forth lower risks and reduced cost; 3) reduction in the operative time and requiring no special carving ability for the surgeon; 4) ability to make high-precision, customized shapes while retaining tissue viability; 5) more widespread access for patients to certain reconstruction procedures, such as ear reconstruction; and 6) removal of concerns of using synthetic prostheses with their associated complications (i.e., the potential need for explanation of synthetic material in the setting of any superficial trauma or infection).

DETAILED DESCRIPTION

The system 100 and method of the present invention are used to fabricate implants 200 for reconstructive surgery. The implant 200 is fabricated for a targeted anatomic area (e.g., ear) using off-the-shelf human cadaveric cartilage or autologous banked cartilage. Similarly, a cartilage tissue from an appropriate donor animal can be used. The method utilizes a 3D freeze micromilling process to sculpt the cartilage into its final, 3D complex form either resembling the specific anatomic part to be produced, or according to a predetermined design that fits the surgical need. Temperature is controlled during the micromilling process to ensure viability of the implant 200. Those temperatures are well below freezing, in the range of about −40 to −10 deg. C.

Figure 1A:
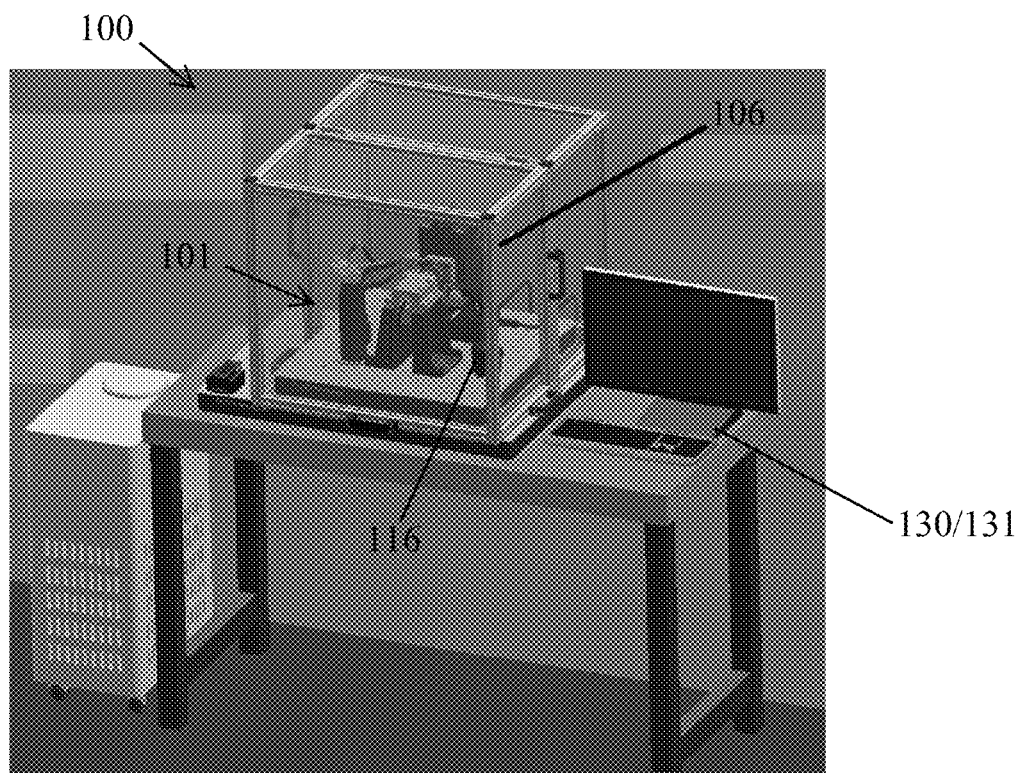
FIGS. 1A-1C show the system according to one embodiment.
Figure 1B:
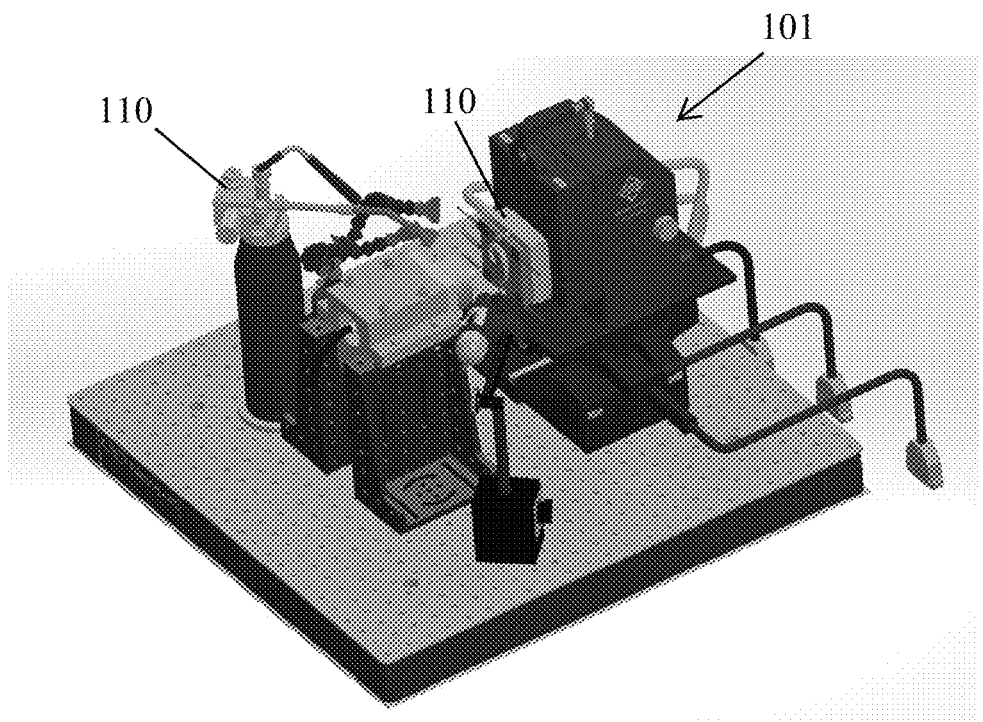
Figure 1C:
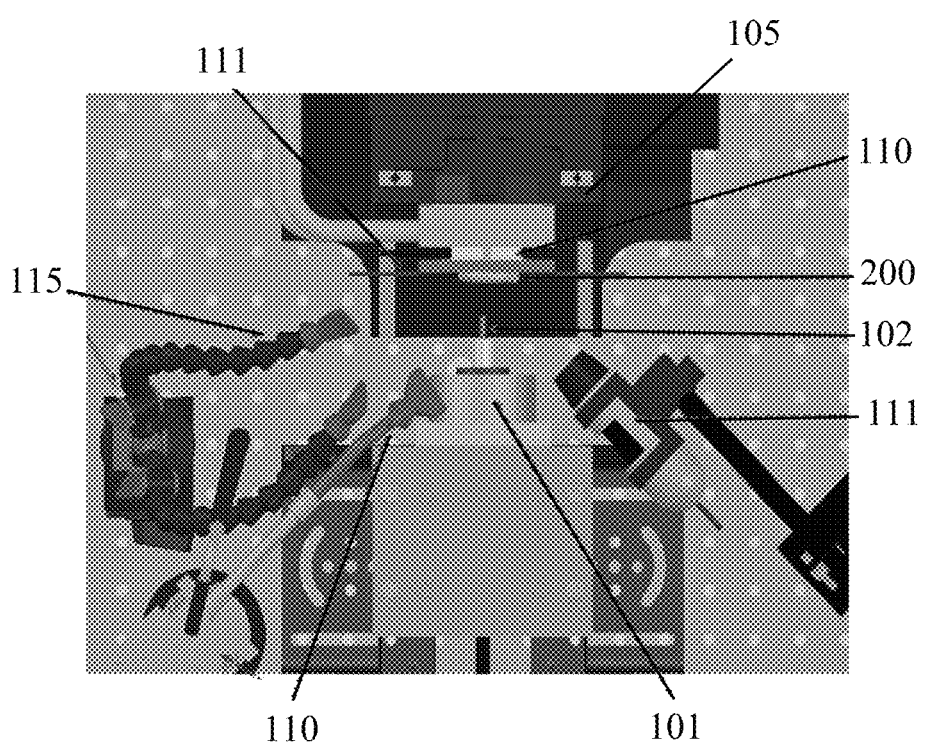

In the embodiment shown in FIGS. 1A-1C, the system 100 comprises a micromilling machine 101 having a cutting tool 102 that shapes cartilage blank to form an implant 200. Different types of cartilage are available for use in medical procedures, including autologous cartilage obtained from the patient and cartilage harvested from a cadaver or other donor, or cartilage from an animal. Cadaveric cartilage is increasingly used by surgeons as it does not require a surgery to harvest tissue from a living patient. The cadaveric cartilage blanks, which are commercially available as a block, sheet, or other generic shapes, may undergo a preparation process that removes identifiable antigens, which could lead to rejection, but leaves the extracellular collagenous and glycoprotein framework intact. The cadaveric cartilage allografts retain much of the structural properties of native cartilage, enabling it to maintain structural stability sufficient for shaping. In addition to these benefits, the use of cadaveric cartilage in humans is well-studied and can allow for biocompatibility and tissue stability. In an alternative embodiment, the system 100 and method can also be used to sculpt a patient's own tissue, including cartilage and other tissues, into any complex design for reimplantation. In this embodiment, the cartilage may be frozen prior to shaping.

Figure 2:
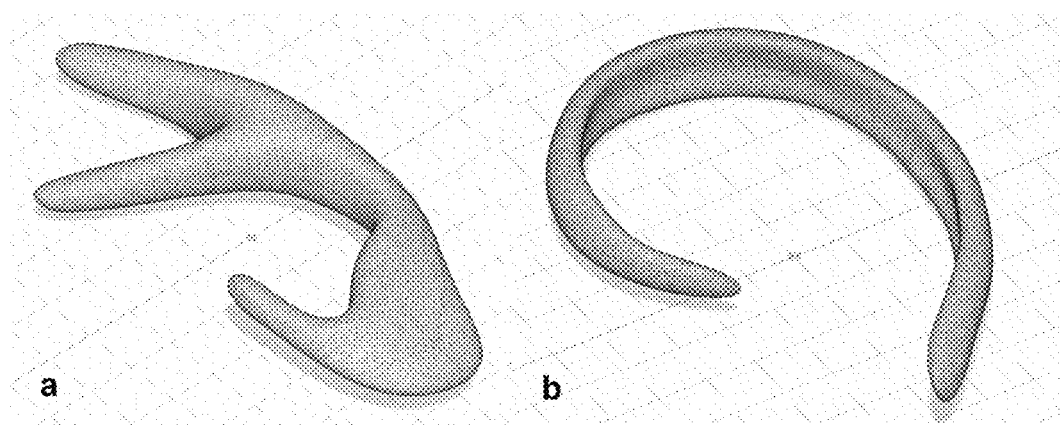
FIG. 2 is a digital representation of an ear implant.

The design of the implant 200 can be created digitally from medical scans and imaging (i.e. computer-aided tomography, magnetic resonance imaging, etc.) or from standardized shapes and sizes of a given anatomic part to be produced. When using medical imaging, the obtained images are converted into virtual solid CAD (computer aided design) models. In both cases, the CAD model of the geometry is altered as needed to design the desired implant 200. This model is converted to create instructions for the micromilling apparatus 101. For example, a digital model of the implant can be used by computer-aided manufacturing (CAM) software to generate a toolpath for the cutting tool 102. The toolpath may comprise a G-code or other instructions known in the art. The instructions are used by the milling machine 101 to carve out the desired geometry from cartilage blanks or raw pieces. FIG. 2 shows digital models of an ear implant 200, including the antihelix and helix of the ear. In an alternative embodiment, a sculpted clay prototype of the implant 200 can be created by a technician then digitized using a high-resolution scanner to create a 3D model of the implant 200.

In the micromachining process, micron-scale cutting tools 102 are used with an ultra-high speed spindle (i.e. speeds greater than 60,000 rpm) for targeted and precise removal of material from the workpiece to achieve the desired geometry. Referring again to FIG. 1B, the micromilling cutting tool 102 has a diameter of about 500 µm, and the micromachining system provides a motion accuracy of about 1 µm. Using a microscale cutting tool 102 enables the micromilling operation to be performed on the cartilage without generating excessive heat, which could destabilize the structural framework of the cartilage. Depending on the amount of micromilling required to shape the implant 200, cutting tools 102 having a diameter of about 50 µm to several millimeters can be used. Larger diameter tools 102 may be used if the temperature of the cartilage is regulated during the milling process. For example, if the cartilage is actively cooled during milling, as in the embodiment shown here, the cutting tool 102 may have a diameter up to several millimeters. The cutting tool 102 may have varying lengths and may include a variety of shapes, such as a square end, ball-end, T-shaped, and other shapes known in the art. This variety in tool sizes, shapes and generated toolpaths allow for the fabrication of many complex planar and 3D geometries.

Given the properties of tissue, using cartilage as a material for micromilling requires the alteration of the common CNC milling process to preserve the biologic integrity of the tissues. The output quality and productivity of the micromachining process are dependent, in part, on the process parameters, including spindle speed, feed rate, and depth of cut. In one example embodiment, the micromachining process has the following parameters: spindle speeds ranging 20,000 rpm-80,000 rpm, feeds ranging 600 mm/min-1800 mm/min, and axial depth of cuts ranging 20 µm-150 µm with two flute micro end-milling tools 102. These parameters can yield the desired form and geometric accuracy, including surface roughness, reduced burr formation, and material removal rate. In addition to process parameters and generated toolpaths, the following micro-end milling tool shapes are used in this example embodiment to achieve the desired shapes and undercuts: 0.04" diameter tungsten carbide flat end-mill, 0.04" diameter tungsten carbide ball end-mill, 300° undercutting tungsten carbide end mill, 0.125" tungsten carbide flat end-mill (facing and roughing operations). Design changes might require the utilization of any other types of micro-milling tools 102. A microscope device is used to observe the toolpath, to detect any possible failure, and to align the initial position of the cutting tool 102.

Figure 4:
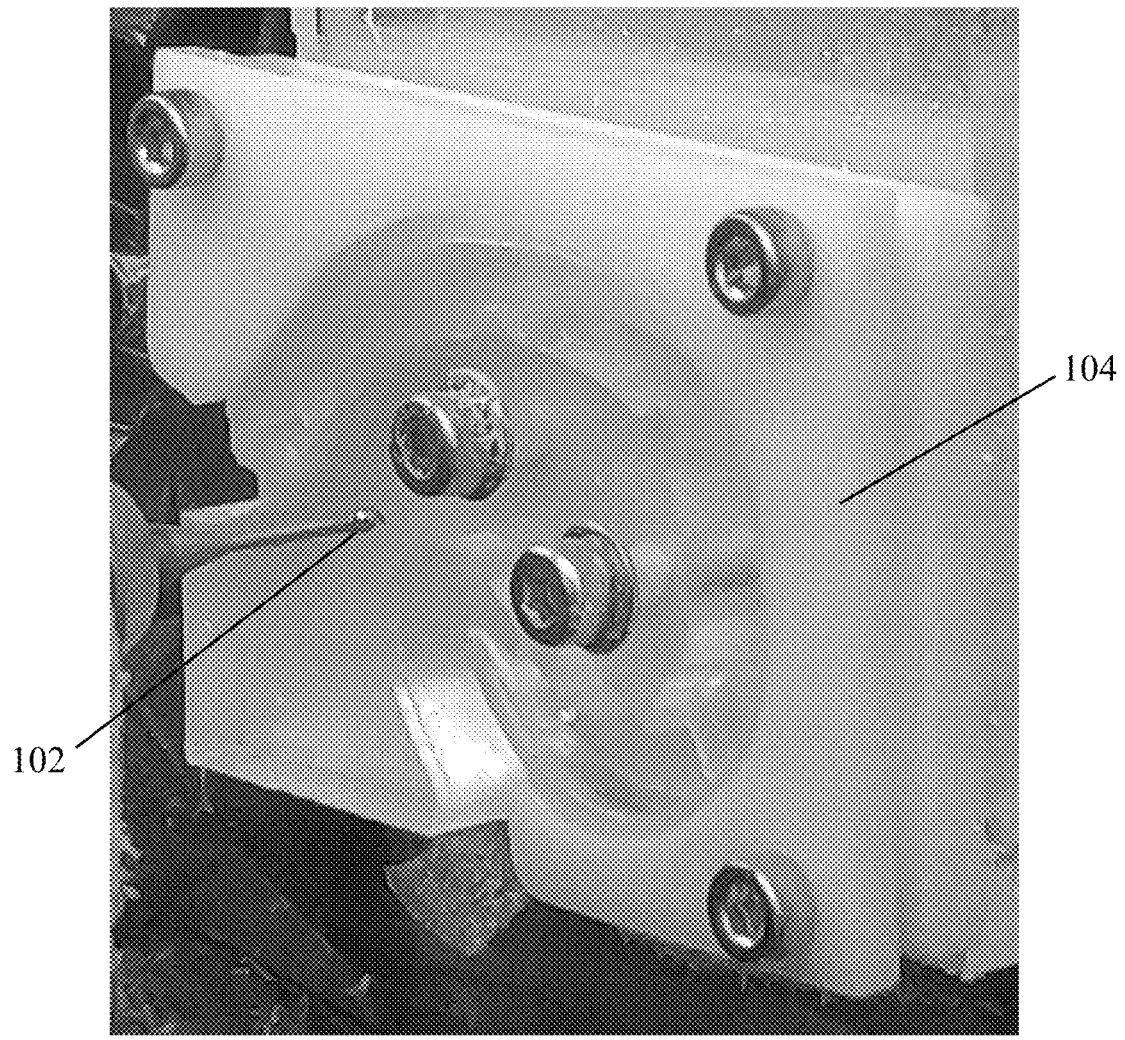
FIG. 4 show a fixture to hold a cartilage blank during a micromilling process.

The cartilage is held during the micromilling process by a fixture 104, which can be fabricated specifically for the shape of the cartilage template using 3D printing or other known methods. In one embodiment, a prototype fixture depicted in FIG. 4, two 3D printed fixtures are screwed from the top and bottom of the cartilage to securely hold the cartilage template. A number of tabs may be included to enable holding the blank during micromilling. In addition, features such as precision pin locations may be used to enable micromachining both sized (top and bottom) of the cartilage if the desired cartilage geometry necessitates such features.

Commercially available cartilage is stored frozen to preserve the cartilage and ensure viability once implanted. The system 100 includes a thermoregulation device 110 and a humidity control device 115 to ensure that the cartilage remains frozen, preventing degradation of the cartilage during milling. Ice formation, "frost", is a detrimental issue for the micromilling process, either damaging the machine parts or interrupting the cutting process. Condensation on the sub-freezing cartilage can be controlled by housing the system 100 in a sealed chamber 106. The sealed chamber 106 further permits the milling operation to be performed in a sterile environment.

As shown in the embodiment depicted in FIG. 1A, the thermoregulation device 110 comprises a liquid-cooled plate mounted to the stage 105 of the milling machine 101. Heat generated by the cutting tool 102 can be removed from the cartilage through conduction, which is mounted to the stage 105 by the fixture 104. By adjusting the flow of fluid through the cooling plate, the stage 105 can be maintained at a temperature below 0 deg. C. or other temperature specified by the cartilage supplier, as low as −40 deg. C. Alternatively, a thermoelectric cooling device, such as a Peltier cooler, may be used in place of or in conjunction with the liquid-cooled plate. FIG. 1B depicts a secondary thermoregulation device 110, which directly cools the cartilage and cutting tool 102. The device 110 shown in FIG. 1B comprises a nozzle controlling a flow of liquid nitrogen directed at the cartilage. In addition to liquid nitrogen, supercooled alcohol, supercritical carbon dioxide, and other similar cryogenic fluids can be used. Additional nozzles may be directed at the cutting tool or other system 100 components. During the micromilling process, the liquid is sprayed onto the surface of the cartilage and/or the tip of the cutting tool 102 for short periods of time. The spray volume and duration can be controlled using the feedback from a temperature sensor 111, such as thermocouples. The spraying prevents local temperature rises on the surface of the cartilage as well as where the micro cutting tool 102 contacts the cartilage surface. In the example embodiment shown in FIGS. 1A-1B, both the liquid-cooled plate and direct cooling nozzle are used as thermoregulation devices 110. The humidity control device 115 comprises a port flowing a cold dry gas, such as air or nitrogen. Other humidity control devices 115 known in the art may be used.

While the thermoregulation device 110 actively cools the cartilage or system 100 components, temperature sensors 111 monitor the temperature to determine whether additional cooling is needed and to ensure that the cartilage remains at an appropriate temperature. The temperature sensor 111 may comprise a thermocouple, infrared sensor, infrared camera, or similar device. An infrared sensor is useful to monitor the temperature of the cartilage, particularly at the site of milling by the cutting tool 102, since direct contact with the measured object is not needed with this type of sensor 111.

The temperature sensor 111 can provide data to a controller 130, which may include a storage device or data log. If a review of the data log indicates that the temperature of the cartilage rose above freezing during any part of the milling process, the implant 200 can be discarded. Similarly, a digital hygrometer 116 can be used to provide data about humidity levels within the chamber. The controller 130 may comprise a microcomputer, a microprocessor, an application specific integrated circuit, a programmable logic array, a logic device, an arithmetic logic unit, a digital signal processor, or another data processor, and supporting electronic hardware and software.

In an alternative embodiment, the thermoregulation device 110 comprises a recirculating chiller (able to reach −30 deg. C.) and a thermoelectric cooler module. Chilled coolant fluid is circulated through isolated tubes to cool down the hot side of the thermoelectric cooler, which uses the Peltier effect to transfer heat using electricity. The coolant generally consists of alcohol based fluids (or any mixture of it with water, in other words antifreeze solutions) such as ethanol, isopropanol, ethylene glycol, polypropylene glycol. Other options may include liquid gases or nanofluid coolants. When the thermoelectric cooler is attached to the chilled coolant on the hot side, it decreases the temperature even lower than −3 deg. C. on the other surface (cold side). The cadaveric cartilage is placed on a custom-design fixture 104, which is attached to the cold side of the thermoelectric cooler. With the customized cooling system, the temperature of the workpiece can be controlled to any value between −5 deg. C. and room temperature. The thermoregulation device 110 may further include a temperature controller 131 (for example, a PID controller or setpoint controller) and multiple thermocouples 111 attached to the cooling assembly. The temperature controller 131 employs feedback control on temperature very accurately (better than 1 deg. C. accuracy). The temperature controller 131 may be part of the main controller 130 or a standalone module.

The thermoregulation device 110 and humidity control device 115 may also be connected to the controller 130, which monitors the data from other sensors (i.e. temperature sensor 111) to determine if the operation is within an acceptable range of temperature and humidity. The controller 130 may adjust the operating parameters to maintain an acceptable temperature and humidity level. For example, the feedback controller 131 has the ability to increase the flow of dry gas, increase the power of the thermoregulation device 110, or increase the flow of liquid through the cooling plate. This thermal controller 131 can be coordinated with the controller 130 of the micromilling machine 101, if desired, to also control spindle speed to reduce the heat generated by the tool.

Figure 5:
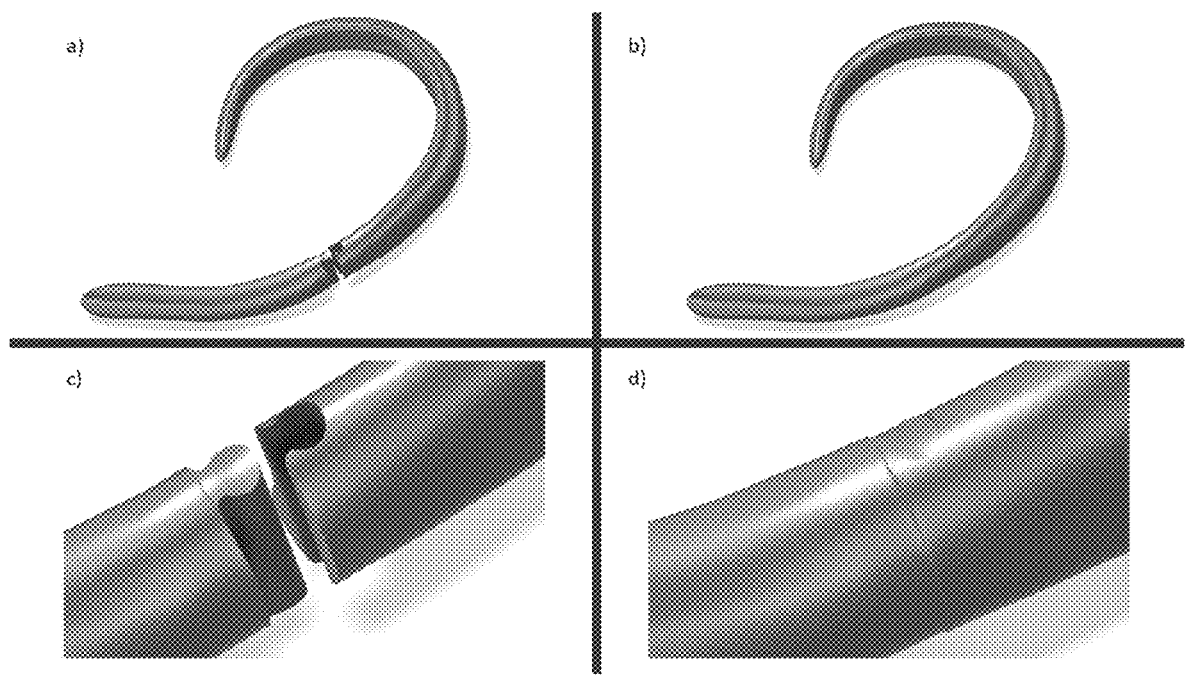
FIG. 5 shows a multipart implant model.

In some cases, the size of the desired 3D geometry of the cartilage implant 200 is larger than the available sizes of the cartilage blanks/pieces. To address this issue, the design of the implant 200 can be modified to include a multi-part modeling approach where the 3D geometry of the implant 200 is divided into smaller portions. In each portion, the implant 200 incorporates matching sides of standardized joining elements (e.g., dovetail or jigsaw puzzle shapes, see FIG. 5), which enables simple yet functionally effective (strength, tissue continuity) assembly of the smaller cartilage pieces into a whole implant 200.

After completing the micromilling process, the sculpted cartilage implant 200 is maintained in a frozen state and preserved until surgery. A surgeon will use the implant 200 similar to the process used in a standard autologous approach. Unlike the standard approach, the implant 200 is pre-formed and extensive manipulation and shaping of the cartilage by the surgeon during surgery will not be necessary. In addition to forming ear cartilage, the system 100 and method can be used to create other custom cartilage implants 200 or to sculpt a patient's own tissue into any complex design prior to implantation.

Figure 3:
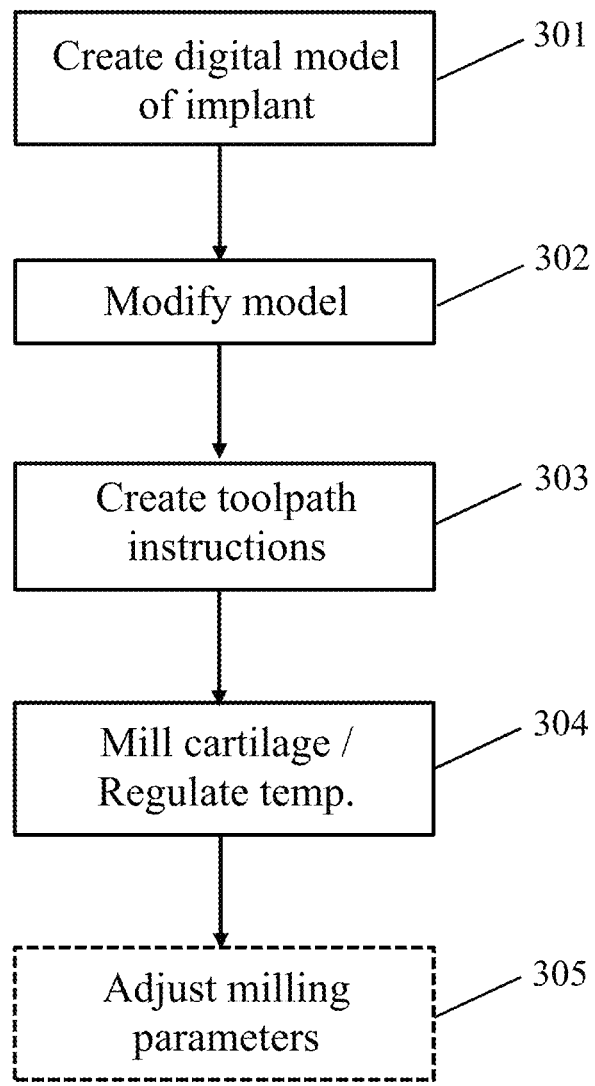
FIG. 3 is a flowchart describing process steps.

FIG. 3 is a flowchart describing the process of fabricating an implant 200, according to one embodiment. First, at step 301, a patient image or standard design is used to create a model of the implant 200. At step 302, the digital model of the implant 200 is modified to create the desired geometry of the implant. Next, at step 303, toolpath instructions are created from the digital model. The instructions can be generated using CAM software. With the cartilage blank positioned on the milling machine 101, the freeze micromilling operation is initiated at step 304. During the freeze micromilling operation, the temperature of the cartilage is regulated using the thermoregulation devices 110 and the humidity is controlled using the humidity control device 115. As noted, the controller 130 may be connected to sensors 111/116 to monitor the environment surrounding the cartilage or other tissue. If the controller 130 identifies an abnormal temperature or humidity reading from the sensors 111/116, then the controller 130 may adjust the temperature and/or humidity through the thermoregulation device 110 or humidity control device 115. For example, if a temperature reading from an infrared temperature sensor 111 indicates that the cartilage is approaching a critical temperature, then the controller 130 will communicate with a pump connected to the liquid-cooled plate, instructing the pump to increase the flow of fluid through the plate. Similarly, at step 305 the controller 130 may adjust operating parameters of the milling machine 101. Parameters may include the speed of the cutting tool 102, the tool path, or the duration of contact between the cutting tool 102 and the cartilage. Adjusting the operating parameters at step 305 is optional and would be implemented if the temperature and humidity regulation at step 304 is not sufficient.

Examples of uses of the system 100 and method include: (i) production of ear implant or parts thereof for patients with ear defects from congenital causes (microtia or anotia) and from acquired injuries (burns, trauma, dog bites, cancer); (ii) production of nose frameworks or parts thereof for patients with nose defects from congenital or acquired causes; (iii) production of specific facial augmentation implants for patients with other facial feature deformities requiring augmentation (e.g., cheek implants, maxillary augmentation implant for cleft lip and palate patients); (iv) production of trapezium-shaped implants for patients needing carpometacarpal arthroplasty who are at risk of thumb collapse after trapezium bone excision; (v) production of any skeletal or cartilaginous hand parts for patients with hand conditions that may benefit customized implant (e.g., phalangeal condyle, part of carpal bone, etc.); (vi) production of customized airway segments for patients with airway deformities who could benefit from structural pieces (e.g., laryngomalacia); (vii) production of any other bodily implants using.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof. In particular, one or more features in any of the embodiments described herein may be combined with one or more features from any other embodiments described herein.

Protection may also be sought for any features disclosed in any one or more published documents referred to and/or incorporated by reference in combination with the present disclosure.

What is claimed is:

1. A system for fabricating an implant from a cartilage blank comprising:
    a milling machine comprising a cutting tool and a stage, wherein the stage is adapted to mount the cartilage blank to the stage;
    at least one temperature sensor generating temperature data;
    a thermoregulation device; and
    a controller that receives the temperature data from the temperature sensor,
    wherein the controller adjusts the thermoregulation device to maintain a pre-determined operating temperature.

2. The system of claim 1, wherein the cartilage blank is selected from the group consisting of human cadaveric cartilage, human donor cartilage, animal donor cartilage, and autologous cartilage.

3. The system of claim 1, wherein the thermoregulation device comprises a liquid-cooled plate mounted to the stage.

4. The system of claim 1, wherein the thermoregulation device comprises a nozzle controlling a flow of a cryogenic fluid.

5. The system of claim 4, wherein the cryogenic fluid is selected from the group consisting of liquid nitrogen, supercooled alcohol, and supercritical carbon dioxide.

6. The system of claim 1, wherein the temperature sensor comprises an infrared sensor that provides temperature data related to a surface of the cartilage blank in contact with the cutting tool.

7. The system of claim 1, wherein the cutting tool has a diameter of less than 2 mm.

8. The system of claim 7, wherein the cutting tool has a diameter of less than 500 µm.

9. The system of claim 1, further comprising a sealed chamber surrounding the cutting tool and stage.

10. The system of claim 1, further comprising:
    a humidity control device connected to the controller.

11. The system of claim 10, wherein the humidity control device comprises a port flowing dry gas.

12. A method of fabricating an implant from cadaveric cartilage comprising:
    generating a digital model of the implant;
    converting the model into instructions for a milling machine, wherein the milling machine is connected to a controller;
    sending the instructions to the controller to initiate milling according to the instructions;
    using the controller, regulating at least one of temperature and humidity.

13. The method of claim 12, further comprising:
    using the controller, adjusting milling parameters to maintain a desired temperature or humidity range.

* * * * *